United States Patent
Kruglick

(10) Patent No.: US 11,398,301 B2
(45) Date of Patent: Jul. 26, 2022

(54) NORMALIZED STANDARD DEVIATION TRANSITION BASED DOSIMETRY MONITORING FOR LASER TREATMENT

(71) Applicant: LUTRONIC VISION INC., Burlington, MA (US)

(72) Inventor: Ezekiel Kruglick, Poway, CA (US)

(73) Assignee: LUTRONIC VISION INC., Burlington, MA (US)

( * ) Notice: Subject to any disclaimer, the term of this patent is extended or adjusted under 35 U.S.C. 154(b) by 14 days.

(21) Appl. No.: 16/962,872

(22) PCT Filed: Feb. 2, 2018

(86) PCT No.: PCT/US2018/016667
§ 371 (c)(1),
(2) Date: Jul. 17, 2020

(87) PCT Pub. No.: WO2019/152048
PCT Pub. Date: Aug. 8, 2019

(65) Prior Publication Data
US 2020/0350055 A1 Nov. 5, 2020

(51) Int. Cl.
*G16H 20/00* (2018.01)
*G16H 20/40* (2018.01)
(Continued)

(52) U.S. Cl.
CPC ........... *G16H 20/40* (2018.01); *A61F 9/0084* (2013.01); *G01N 21/1702* (2013.01);
(Continued)

(58) Field of Classification Search
CPC ............ A61F 2009/00844; A61F 9/008; A61F 9/00821; A61F 9/00814; A61F 9/00823;
(Continued)

(56) References Cited

U.S. PATENT DOCUMENTS 7,441,901 B2 10/2008 Liang
9,662,006 B2 5/2017 Dai et al.
(Continued)

FOREIGN PATENT DOCUMENTS

WO 0040144 A1 7/2000

OTHER PUBLICATIONS

International Search Report and Written Opinion for International Application No. PCT/US2018/016667 dated Apr. 13, 2018, pp. 7.

*Primary Examiner* — Rex R Holmes
*Assistant Examiner* — Sana Sahand

(57) ABSTRACT

Technologies are generally described for normalized standard deviation transition based dosimetry monitoring for laser treatment. In some examples, a response signal may be generated based on a physical response to a laser pulse detected through acoustic or optical means. Each response signal may be a time series of data with a number of points. Standard deviation may be determined for each response signal and normalized using a mean or comparable normalization factor. Thus, a robust distribution may be computed from the response to each laser pulse. A change in the normalized standard deviation from each single pulse's time domain response data may be used to determine how many laser pulses remain before completion of the treatment (similar to event onset response). Thus, laser treatment may be continued based on an estimation of remaining pulses for completion or ceased if completion is reached.

6 Claims, 8 Drawing Sheets

(51) Int. Cl.
  *A61F 9/008* (2006.01)
  *G01N 21/17* (2006.01)
  *G01N 21/55* (2014.01)

(52) U.S. Cl.
  CPC .... *G01N 21/55* (2013.01); *A61F 2009/00897* (2013.01); *G01N 2021/1706* (2013.01)

(58) Field of Classification Search
  CPC .................. A61F 9/0084; A61F 9/009; A61F 2009/00851; A61F 2009/00868; A61F 2009/00891
  See application file for complete search history.

(56)  References Cited

U.S. PATENT DOCUMENTS

2003/0036751 A1* 2/2003 Anderson ............. A61B 34/71
      606/9
  2006/0217691 A1* 9/2006 Schuele ............. A61F 9/00821
      606/12
  2016/0038025 A1  2/2016 Irsch et al.
  2016/0038277 A1  2/2016 Dai et al.

* cited by examiner

COMPUTER PROGRAM PRODUCT 800

SIGNAL BEARING MEDIUM 802

804 ONE OR MORE INSTRUCTIONS TO:

RECEIVE A PLURALITY OF RESPONSE SIGNALS CORRESPONDING TO A PLURALITY OF LASER PULSES DIRECTED TO A TREATMENT AREA AS PART OF THE LASER TREATMENT;

DETERMINE A STANDARD DEVIATION FROM EACH RESPONSE SIGNAL FOLLOWING A RECEIPT OF EACH OF THE PLURALITY OF RESPONSE SIGNALS;

FOLLOWING THE RECEIPT OF EACH RESPONSE SIGNAL, DERIVE A NORMALIZED STANDARD DEVIATION BY DIVIDING THE STANDARD DEVIATION BY AN ARITHMETIC MEAN OF EACH OF THE PLURALITY OF RESPONSE SIGNALS; AND/OR

DETERMINE A NUMBER OF LASER PULSES REMAINING TO COMPLETE THE LASER TREATMENT FOR EACH RESPONSE SIGNAL BASED ON THE NORMALIZED STANDARD DEVIATION FOLLOWING THE RECEIPT OF EACH RESPONSE SIGNAL.

| COMPUTER-READABLE MEDIUM 806 | RECORDABLE MEDIUM 808 | COMMUNICATIONS MEDIUM 810 |

FIG. 8

NORMALIZED STANDARD DEVIATION TRANSITION BASED DOSIMETRY MONITORING FOR LASER TREATMENT

CROSS-REFERENCE TO RELATED APPLICATIONS

The present application is a U.S. National Stage filing under 35 U.S.C. § 371 of International Application PCT/US2018/016667, filed Feb. 2, 2018 and entitled "NORMALIZED STANDARD DEVIATION TRANSITION BASED DOSIMETRY MONITORING FOR LASER TREATMENT." The International Application, including any appendices or attachments thereof, is incorporated by reference herein in its entirety.

BACKGROUND

Unless otherwise indicated herein, the materials described in this section are not prior art to the claims in this application and are not admitted to be prior art by inclusion in this section.

Treatment of a number of diseases, such as eye diseases, through laser application is a common approach. Tears or growths on the retina, and other diseases may be treated by application of laser beams (e.g., laser pulses) to the treatment site. To gauge an effect of the laser treatment, dosimetry may be performed using acoustic detection or reflectometry, where the intensity of reflections of the laser pulse may be measured in real time. Laser beams generate heat at the treatment site, which in turn may result in formation of bubbles (through the expansion of fluids transforming into gases). Formation of the bubbles may be detected through acoustic or optical observation and treatment continued or ceased based on the observation. Signals used for detection may be complex and include substantial background noise. Thus, programmatic interpretation of time-series data may be problematic in the absence of a robust metric.

SUMMARY

The present disclosure generally describes techniques related to normalized standard deviation transition based dosimetry monitoring for laser treatment.

According to some examples, a method for normalized standard deviation transition based dosimetry monitoring of a laser treatment is described. The method may include receiving a plurality of response signals corresponding to a plurality of laser pulses directed to a treatment area as part of the laser treatment; determining a standard deviation from each response signal following a receipt of each of the plurality of response signals; deriving a normalized standard deviation by dividing the standard deviation by an arithmetic mean of each of the plurality of response signals following the receipt of each response signal; and determining a number of laser pulses remaining to complete the laser treatment for each response signal based on the normalized standard deviation following the receipt of each response signal.

According to other examples, an apparatus for normalized standard deviation transition based dosimetry monitoring of a laser treatment is described. The apparatus may include a detector configured to detect a plurality of responses from a treatment area upon application of a plurality of laser pulses to the treatment area as part of the laser treatment and derive a plurality of response signals from the plurality of responses corresponding to the plurality of laser pulses directed to the treatment area. The apparatus may further include a processor coupled to the detector and configured to determine a standard deviation from each response signal following a receipt of each of the plurality of response signals; following the receipt of each response signal, derive a normalized standard deviation by dividing the standard deviation by an arithmetic mean of each of the plurality of response signals; and determine a number of laser pulses remaining to complete the laser treatment following the receipt of a response signal based on the normalized standard deviation.

According to further examples, a laser treatment system for normalized standard deviation transition based dosimetry monitoring is described. The system may include a laser source configured to direct a plurality of laser pulses to a treatment area as part of a laser treatment and a detector configured to detect a plurality of responses from the treatment area upon application of the plurality of laser pulses to the treatment area; and derive a plurality of response signals from the plurality of responses corresponding to the plurality of laser pulses directed to the treatment area. The system may also include an estimator coupled to the detector and configured to determine a standard deviation from each response signal following a receipt of each of the plurality of response signals; following the receipt of each response signal, derive a normalized standard deviation by dividing the standard deviation by an arithmetic mean of each of the plurality of response signals; and determine a number of laser pulses remaining to complete the laser treatment for each response signal based on the normalized standard deviation following the receipt of each response signal.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The foregoing and other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

FIG. 8 illustrates a block diagram of an example computer program product, some of which are arranged in accordance with at least some embodiments described herein.

DETAILED DESCRIPTION

Figure 1:
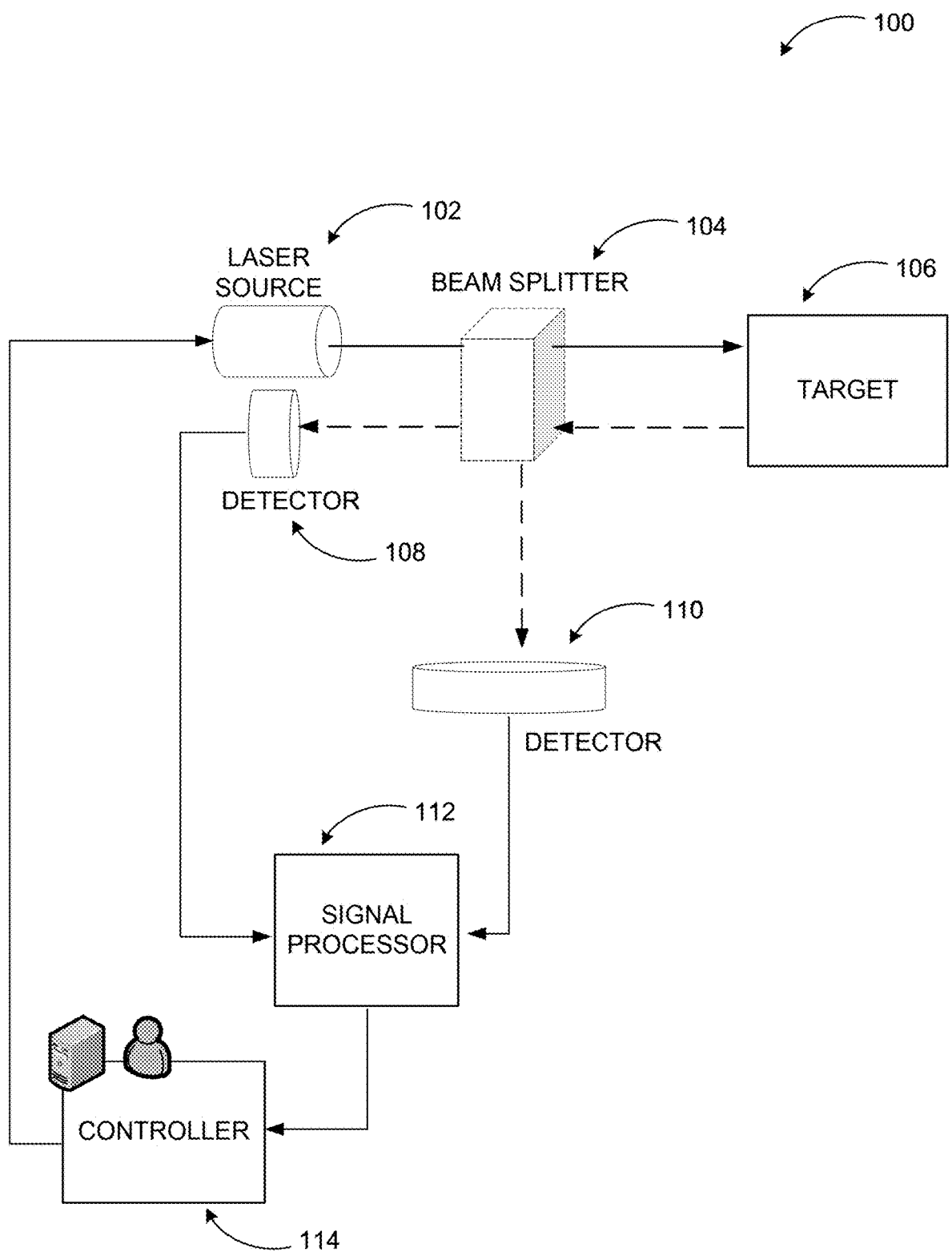
FIG. 1 includes a conceptual illustration of a system to implement normalized standard deviation transition based dosimetry monitoring of laser treatments.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. The aspects of the present disclosure, as generally described herein, and illustrated in the Figures, can be arranged, substituted, combined, separated, and designed in a wide variety of different configurations, all of which are explicitly contemplated herein.

This disclosure is generally drawn, inter alia, to methods, apparatus, systems, devices, and/or computer program products related to normalized standard deviation transition based dosimetry monitoring for laser treatment.

Briefly stated, technologies are generally described for normalized standard deviation transition based dosimetry monitoring for laser treatment. In some examples, a response signal may be generated based on a physical response to a laser pulse detected through acoustic or optical means. Each response signal may be a time series of data with a number of points. Standard deviation may be determined for each response signal and normalized using a mean or comparable normalization factor. Thus, a robust distribution may be computed from the response to each laser pulse. A change in the normalized standard deviation from each single pulse's time domain response data may be used to determine how many laser pulses remain before completion of the treatment (similar to event onset response). Thus, laser treatment may be continued based on an estimation of remaining pulses for completion or ceased if completion is reached.

FIG. 1 includes a conceptual illustration of a system to implement normalized standard deviation transition based dosimetry monitoring of laser treatments, arranged in accordance with at least some embodiments described herein.

As shown in diagram 100, a laser treatment system may include a laser source 102 providing laser pulses of defined strength, width, and frequency to a target 106 (treatment area). A physical response of the target 106 may be detected through a detector 108. Detector 108 may generate an electrical response signal corresponding to the physical response and provide to a signal processor 112. In some examples, a portion of the applied laser pulse may be directed to another detector 110 by a beam splitter 104 and a signal generated from the portion of the applied laser pulse by the other detector 110 may also be provided to the signal processor 112 for comparison or calibration purposes. The signal processor 112 may provide an input to a controller 114, which may be a device for automated control of the laser source 102 or a human controller/observer for manual control of the laser source 102.

In an example scenario, the laser treatment may be laser surgical treatment of melanosomes, an abnormal growth on the retina of an eye. Thus, the target 106 may be a portion of the retina. The applied laser beams may generate heat at the treatment site, which in turn may result in formation of bubbles (through the expansion of fluids within the cells transforming into gases) on the retina. The physical response (formation of the bubbles) may be detected acoustically through detection of pressure waves in vitreous fluid or optically (through Doppler interferometry or reflectometry based on relatively large refractive index difference between bubbles and the surrounding fluid). In acoustic measurements, amplitudes or the pressure waves may be relatively small. Furthermore, detection sensors and interface (e.g., cornea) may further reduce the sensitivity in such measurements resulting in high noise level signals. In optical detection, a few bubbles may be created in a small area compared to a laser spot size. Thus, the reflection signal due to the bubbles may be confounded with background emissions (surrounding cells), reflections within the eye, and other factors, again resulting in a relatively low signal-to-noise ratio in the measurement system. In the absence of an accurate metric to interpret the response signals, a doctor may have to rely on observation of the treatment area to determine completion of the treatment, but it may be too late in some cases to stop the treatment or the treatment may be ceased prematurely with unsatisfactory results.

A system according to embodiments may estimate a number of remaining laser pulses before completion of treatment based on determination of a normalized standard deviation for each response signal. In some embodiments, the normalized standard deviation may be evaluated for a given laser pulse (response signal) compared to a previous pulse (e.g., generation of a Markov state tree) to provide even stronger estimation. In other embodiments, an estimator may determine, based on the normalized standard deviation transition between pulses, a number of remaining pulses for completion of the treatment and automatically control the laser source eliminating a need for manual observation and control of the surgical system. In some embodiments, the number of remaining pulses for completion of the treatment may be determined to be zero.

Figure 2:
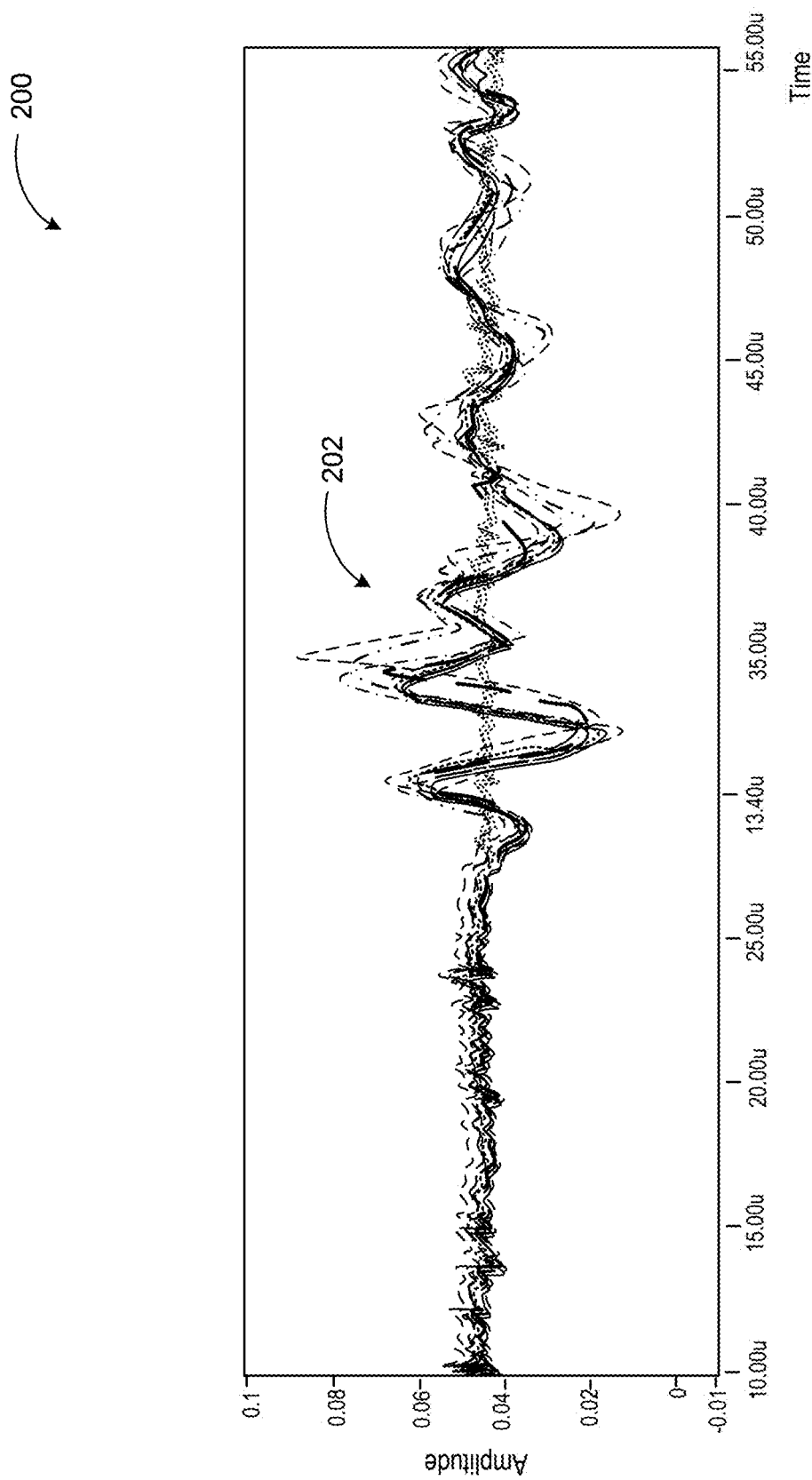
FIG. 2 illustrates an example plot of time-domain acoustic treatment response signals for a laser eye treatment system.

FIG. 2 illustrates an example plot of time-domain acoustic treatment response signals for a laser eye treatment system.

Diagram 200 shows an example ultrasonic output 202 from 15 consecutive laser pulses applied to a treatment area. As the diagram shows, measuring peak amplitude, for example, may be impacted by spurious sensor spikes. Measuring energy may provide a more stable reading, but may be subject to offset drift. As discussed previously, a response signal may be generated based on a physical response to a laser pulse detected through acoustic or optical means. Each response signal in the plot may be a time series of data with a number of points. Standard deviation may be determined from each response signal and normalized using a mean or comparable normalization factor. Thus, a robust distribution may be computed from the response to each laser pulse. A change in the normalized standard deviation from each single pulse's time domain response data may be used to estimate how many laser pulses remain before completion of the treatment, and the laser treatment may be continued based on the estimation of remaining pulses for completion or ceased if completion is reached.

While acoustic and optical detection of the physical response to applied laser pulses are discussed as examples of response detection herein, embodiments are not limited to specific acoustic or optical detection techniques. Any means of detection of the physical response may be used in implementation of normalized standard deviation transition based dosimetry monitoring for laser treatment. For example, optical coherence tomography (OCT), Fabry-Perot techniques, other interferometric techniques, other optical techniques, or other methods may also be used.

Some examples include methods for laser treatment of a treatment area, for example of an eye. Example methods may include receiving a plurality of response signals corresponding to a plurality of laser pulses directed to the treatment area as part of the laser treatment. Example methods may include determining a number of laser pulses remaining to complete the laser treatment after a particular response signal is received, e.g., based on a comparison of one or more response signals with one or more, e.g., previously received response signals. For example, a property, such as a statistical property, of the response signals or a sub-set thereof may be monitored, for example over time, e.g., after each or some number of response signals is/are received, or otherwise at intervals. A property of the response signals may be compared for response signals received during different periods of time. For example, a property (such as statistical property) of a first plurality of response signals may be compared with an analogous property of a second plurality of response signals, and used to determine a number of laser pulses remaining to complete the laser treatment. In some examples, a method may further include stopping the laser treatment (e.g., immediately) if damage is detected in the treatment area (for example, bubble formation), for example using acoustic, optical, or any other appropriate method.

Examples also include equipment configured to perform laser treatment of a treatment area, for example of the eye. Example equipment may be configured to receive response signals corresponding to a plurality of laser pulses directed to the treatment area. Example equipment may be configured to determine a number of laser pulses remaining to complete the laser treatment after a particular response signal is received. Example equipment may comprise an electronic circuit, for example, comprising a processor, configured to determine one or more statistical properties of a plurality of response signals. Example equipment may be configured to compare a property of one or more response signals with one or more previously received response signals. For example, a property, such as a statistical property, of the response signals or a sub-set thereof may be monitored, for example over time or otherwise at intervals. A property of the response signals may be compared for response signals received during different periods of time. For example, equipment may be configured to compare a property (such as statistical property) of a first plurality of response signals with an analogous property of a second plurality of response signals, and to determine a number of laser pulses remaining to complete the laser treatment. In some examples, example equipment may further be configured to stop the laser treatment if damage (e.g., bubble formation in the retina of an eye) is detected, for example, using acoustic, optical, or any other appropriate damage detection sensors. Example equipment may be configured to detect damage in the treatment area, and to stop operation (e.g., immediately) on detection of the damage. For example, the equipment may comprise a photoacoustic sensor, and be configured to stop operation on detection of a photoacoustic signal indicative of bubble formation in the retina of an eye.

Figure 3:
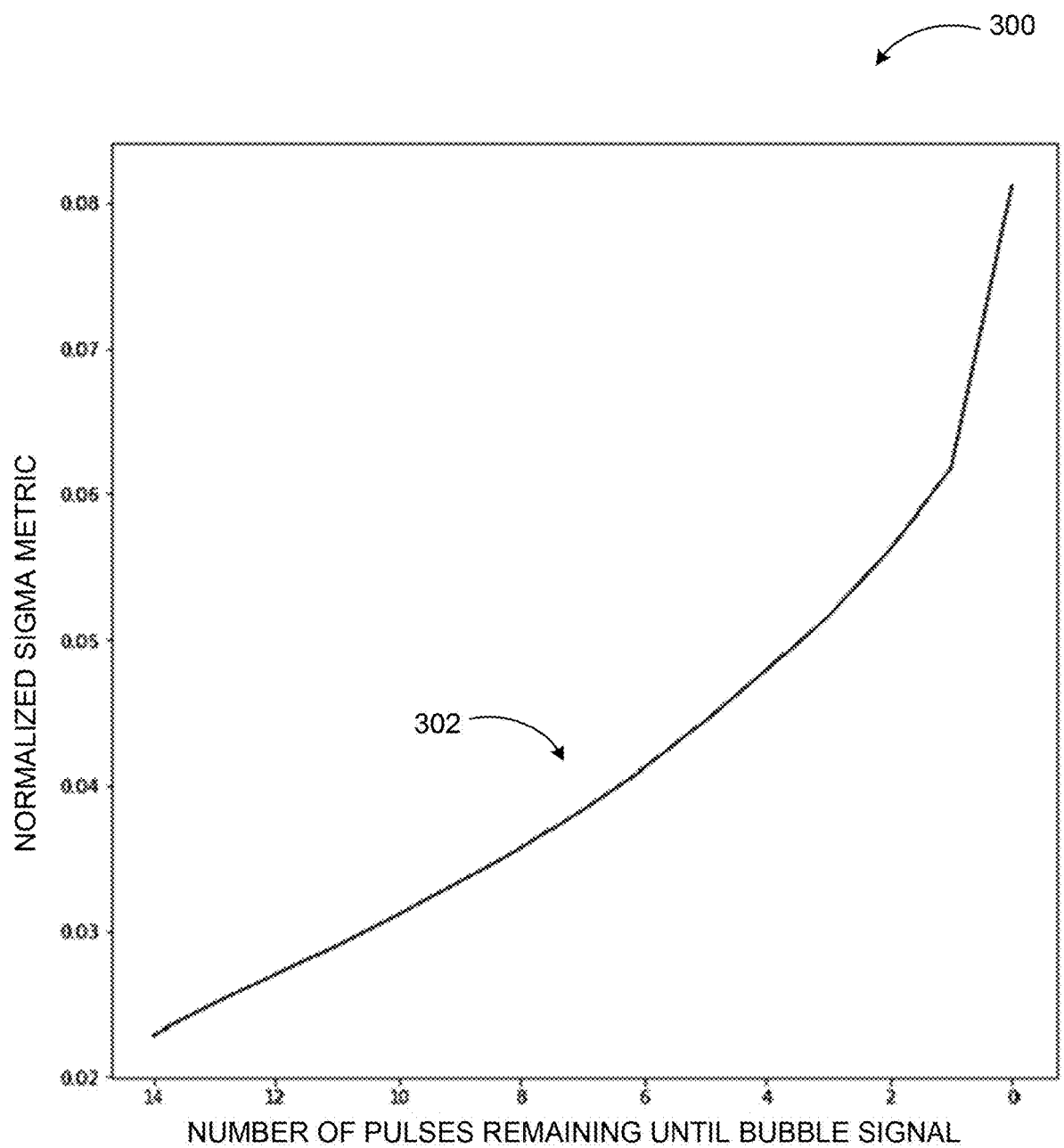
FIG. 3 illustrates an example average normalized standard deviation metric curve for normalized standard deviation transition based dosimetry monitoring of laser treatments.

FIG. 3 illustrates an example average normalized standard deviation metric curve for normalized standard deviation transition based dosimetry monitoring of laser treatments, arranged in accordance with at least some embodiments described herein.

Diagram 300 shows the average normalized standard deviation (sigma) metric 302 for example possible numbers of pulses remaining in a laser treatment regimen as determined from an example sample population. According to some examples, the metric 302 may be interpreted as the normalized standard deviation and may be expected to be around 0.03 when there are about ten laser pulses left before acoustic endpoint (acoustic detection of treatment completion) in the sample population. Moreover, the normalized standard deviation may be expected to rise to around 0.06 (i.e., 100% higher) as a shot reaches two pulses predicted as remaining before the acoustic endpoint.

The normalized standard deviation metric may be considered for bimodal or event onset response phenomena (e.g., formation of bubbles in an eye laser treatment or other treatments where a sudden change signifies completion). In imaginary ideal bimodal phenomena, the detected phenomena (light or sound output) may suddenly jump from very little to a lot when an input stimulus passes a clearly defined critical level.

On the other hand, response may build up as the input stimulus passes through a critical input range in real phenomena. In most real phenomena, the physical responses may vary, for example in laser ophthalmologic treatment, as light absorption varies or fluids convect even with a tightly controlled input laser power. Thus, a single laser pulse may generate a stimulus that may vary with time over a first range and a detection that may also vary in time within a second range. Some approaches may perform detection based on amplitude (of the response signal) alone. To avoid false positives, detection of the stimulus reaching a predefined level may be selected at a high enough amplitude. However, this form of detection may not provide continuous measurement of progress below the threshold.

Normalized standard deviation transition is based on detection of a slope change of the stimulus-to-detection relationship. A Gaussian spread of the detected phenomena may increase as the transition is approached. Thus, the phenomena may be evaluated while filtering out overall power level drift in the signal via the normalized standard deviation, which may effectively measure the local slope of the response curve while removing undesired effects. Therefore, the metric plot in diagram 300 shows the normalized standard deviation providing data that matches expected slope changes of the bimodal function. Using normalized standard deviation, data may be obtained on progress (e.g., of laser treatment) before a full transition to a second state occurs in a bimodal system. Furthermore, greater sensitivity may be achieved closer to the transition.

Figure 4:
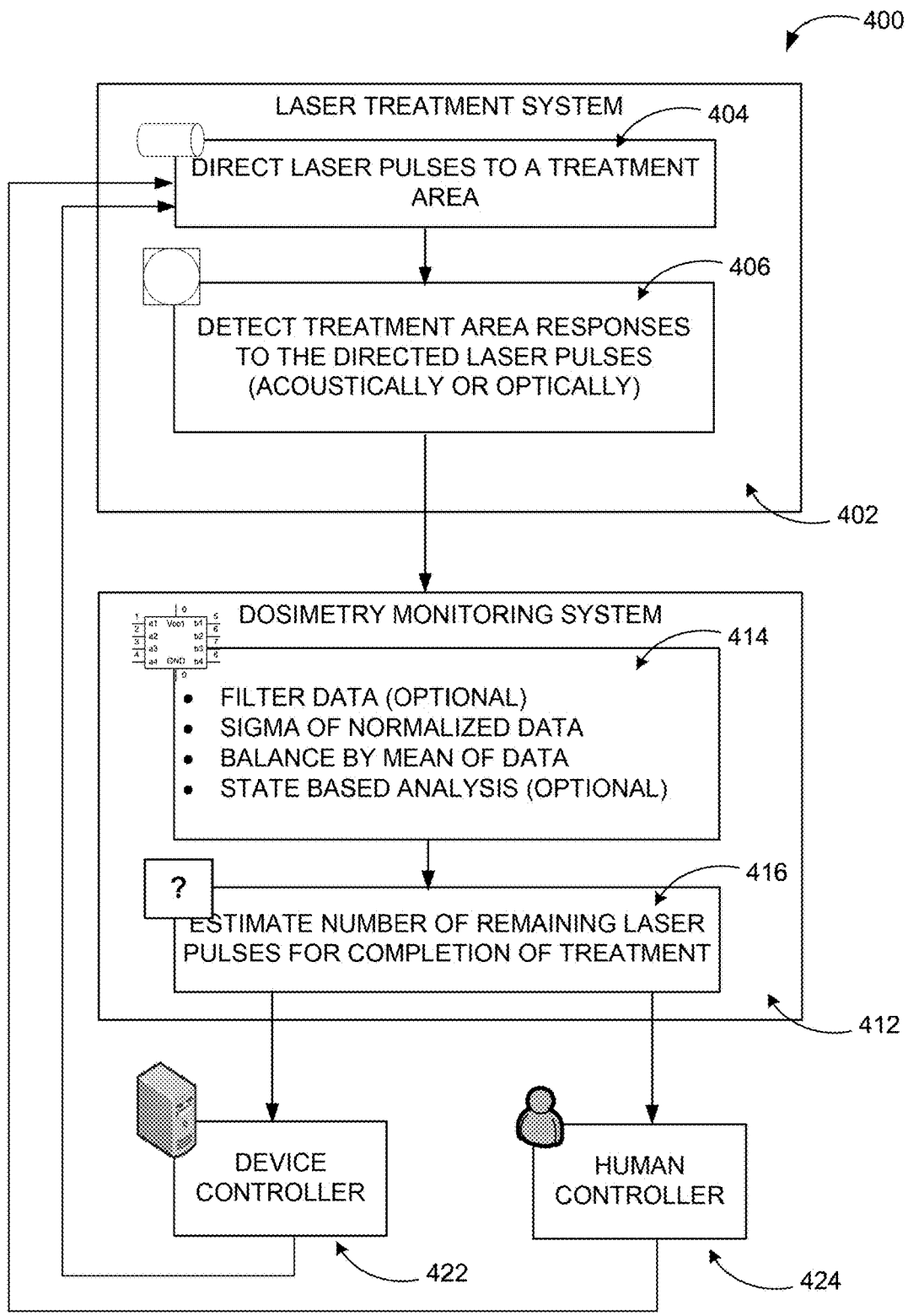
FIG. 4 includes a conceptual block diagram of a system and a method to provide normalized standard deviation transition based dosimetry monitoring of laser treatments.

FIG. 4 includes a conceptual block diagram of a system and a method to provide normalized standard deviation transition based dosimetry monitoring of laser treatments, arranged in accordance with at least some embodiments described herein.

Diagram 400 shows a laser treatment system 402 that includes a laser source 404 configured to direct laser pulses to a treatment area and a detector 406 configured to detect acoustically or optically treatment area responses to the directed laser pulses. A dosimetry monitoring system 412 may include a signal processor 414 configured to optionally filter received response data, compute a standardized deviation of the data, and balance the standard deviation using a mean of the data (e.g., arithmetic mean, median, other representation of the general value range). The signal processor 414 may also perform a state based analysis. The dosimetry monitoring system 412 may also include an estimator 416 configured to estimate a number of remaining laser pulses for completion of the treatment. An output of the dosimetry monitoring system 412 (e.g., the number of remaining pulses for completion of the treatment) may be provided to a human controller 424 or a device controller 422 for automatic control of the laser source 404 (e.g., ceasing the treatment or directing additional laser pulses to the treatment area based on the number of remaining laser pulses).

When a laser pulse is applied to a treatment area, a physical response may occur such as formation of bubbles at the retina in response to treatment of melanosomes in the eye. The physical (or biological) response may be detected through different means such as acoustic detection of pressure waves created by the formation of the bubbles, optical detection of pressure waves using Doppler interferometry, optical detection of the bubble formation through reflectometry, etc. Each detection method may result in generation of an electrical signal or "response signal", which may be processed to determine a course of treatment based on the detected response. In practical implementations, the response signals may be in time domain, which may then be transformed into frequency domain for further processing, in some examples. Thus, for each response signal (corresponding to a physical response to an applied laser pulse), an amplitude, an intensity, a root mean square (rms) signal amplitude, a phase, a frequency, etc. may be measured. In the specific case of optical response signals, interference, beam distribution, speckle may be additional quantities that may be measured.

In some examples, additional determinations, such as variance (square root of standard deviation), mean absolute deviation, median deviation, etc. may also be used. Furthermore, normalization may be performed using arithmetic mean, geometric mean, median, or mean excluding outliers (e.g., excluding spurious responses beyond a certain standard deviation). In other examples, metrics such as linear least-squares, absolute energy of time series, autocorrelation of time series, correlation of maxima or minima, sum of time series values, entropy of x values, peak counting and comparable metrics may be used in place of or in addition to the normalized standard deviation approach. Each approach may vary in accuracy, computational burden, and other aspects.

Thus, a value that is preserved after each response to a laser pulse is received may be described as the sigma-norm herein. In some examples, this represents the normalized standard deviation from each single pulse's time domain response data. The sigma-norm may be computed for each pulse individually. In some examples, after each therapeutic laser pulse is directed towards the eye, the standard deviation of the plurality of response signal values may be determined.

As mentioned above, the signal processor 414 may optionally perform a state based analysis, for example, using Markov or Bayesian state based sigma-norm analysis. The sigma-norm may be evaluated for a given pulse compared to the previous pulse of the same shot to provide even stronger evaluation (e.g., Markov state tree). Such a tree may be a series of states that each indicate potential states of the physiologic process and rules for transitioning among the states based on the observed sigma-norm. Because the sigma-norm provides many different detectable levels leading up to the endpoint (completion of treatment), embodiments may allow treatment to be set at a wide variety of power levels. In some examples, Not-a-Number (NaN) data that may be caused by early sensor deactivation or other errors may be removed from the computation. For example, initial pulse response may be removed to stabilize the computation.

Figure 5:
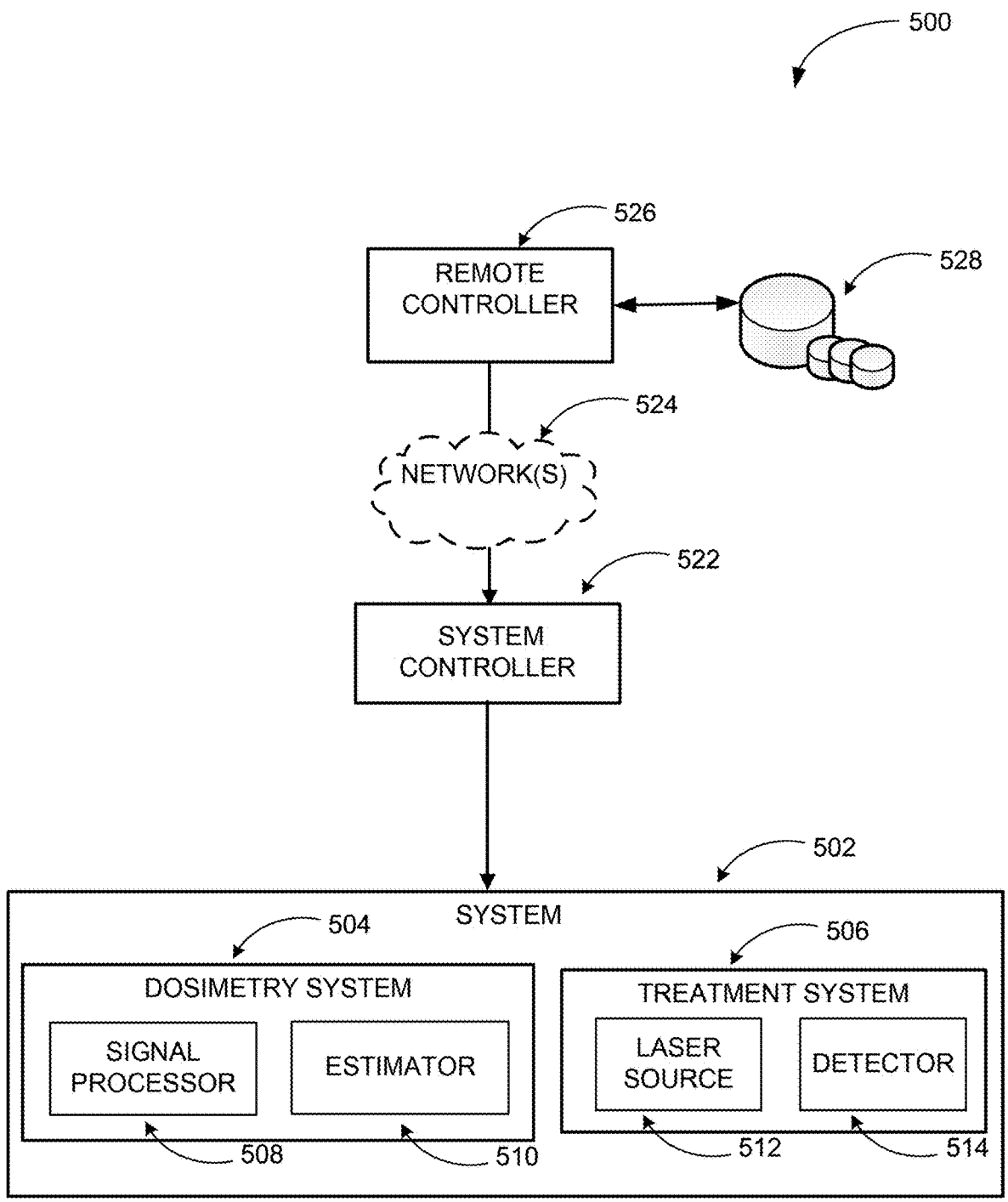
FIG. 5 illustrates major components of an example system configured to provide normalized standard deviation transition based dosimetry monitoring of laser treatments.

FIG. 5 illustrates major components of an example system configured to provide normalized standard deviation transition based dosimetry monitoring of laser treatments, arranged in accordance with at least some embodiments described herein.

As shown in diagram 500, an example system 502 may include a treatment system 506 and a dosimetry system 504 similar to FIG. 4. The treatment system may include a laser source 512 and a detector 514. The laser source 512 may include a semiconductor laser diode, a super-luminescent laser diode, a chemical laser, a gas laser, a solid-state laser, or an optical fiber diode, for example. Various optical components such as lenses and mirrors (not shown) may be used to focus, direct, and otherwise manipulate the laser beam to the treatment site. If the treatment stimulus is to be a different type such as ultrasound or microwave, a different type of source may be used. Detector 514 may include, in optical detection implementations, a photodiode, an active-pixel sensor (APS), a Cadmium Zinc Telluride radiation detector, a charge-coupled device (CCD), a Mercury Cadmium Telluride detector, a reverse-biased light emitting diode (LED), a photoresistor, a phototransistor, or a quantum dot photoconductor, for example. If the detection is to be other than return optical signal, the detector 514 may be acoustic, magnetic, thermal, or any other detector type appropriate to the desired detection phenomena.

Dosimetry system 504 may include a signal processor 508 to filter, process, and manipulate response data received from the detector 514. Signal processor 508 may also determine the normalized standard deviation or other metric. Estimator 510 may estimate a number of remaining laser pulses or other dosing for completion of the treatment based on the normalized standard deviation metric, which may be used to control further operations of the laser source 512.

An example system 502 may be managed by a system controller 522, which may be an on-board special purpose processor, a server, or any other type of controller. In some examples, a remote controller 526 may manage at least some of the operations of the system 502 by communicating with the system controller 522 over one or more wired or wireless networks 524. Data associated with the operations of the system 502 such as treatment response data, patient specific data, and other information may be stored at data store(s) 528.

According to some examples, the signal processor 508 may receive a plurality of response signals corresponding to a plurality of laser pulses directed to a treatment area as part of the laser treatment, compute a standard deviation from each response signal following a receipt of each of the plurality of response signals, and derive a normalized standard deviation by dividing the standard deviation by an arithmetic mean of each response signal following the receipt of each response signal. The signal processor 508 or the estimator 510 may then determine a number of laser pulses remaining to complete the laser treatment for each response signal based on the normalized standard deviation following the receipt of each response signal.

According to other examples, the number of laser pulses remaining to complete the laser treatment for each response signal may be determined based on a change in the normalized standard deviation between two consecutive response signals. A first response signal may be removed from the computation of the standard deviation and the arithmetic mean. The response from the treatment area may be detected acoustically or optically such as through opto-reflectometry. The laser source 512 that directs the plurality of laser pulses to the treatment area may be automatically controlled to cease direction of laser pulses upon completion of the laser treatment based on the remaining number of laser pulses. An optional state based analysis of the change in the normalized standard deviation may be performed using a Markov state based analysis or a Bayesian state based analysis. An (e.g., entropy-based) decision tree may be generated in the state based analysis based on the normalized standard deviation to determine the number of laser pulse remaining for the completion of the laser treatment.

The examples provided in FIG. 1 through FIG. 5 are illustrated with specific systems, devices, applications, and scenarios. Embodiments are not limited to environments according to these examples. Normalized standard deviation transition based dosimetry monitoring for laser treatment may be implemented in environments employing fewer or additional systems, devices, applications, and scenarios. Furthermore, the example systems, devices, applications, and scenarios shown in FIG. 1 through FIG. 5 may be implemented in a similar manner with other user interface or action flow sequences using the principles described herein.

Figure 6:
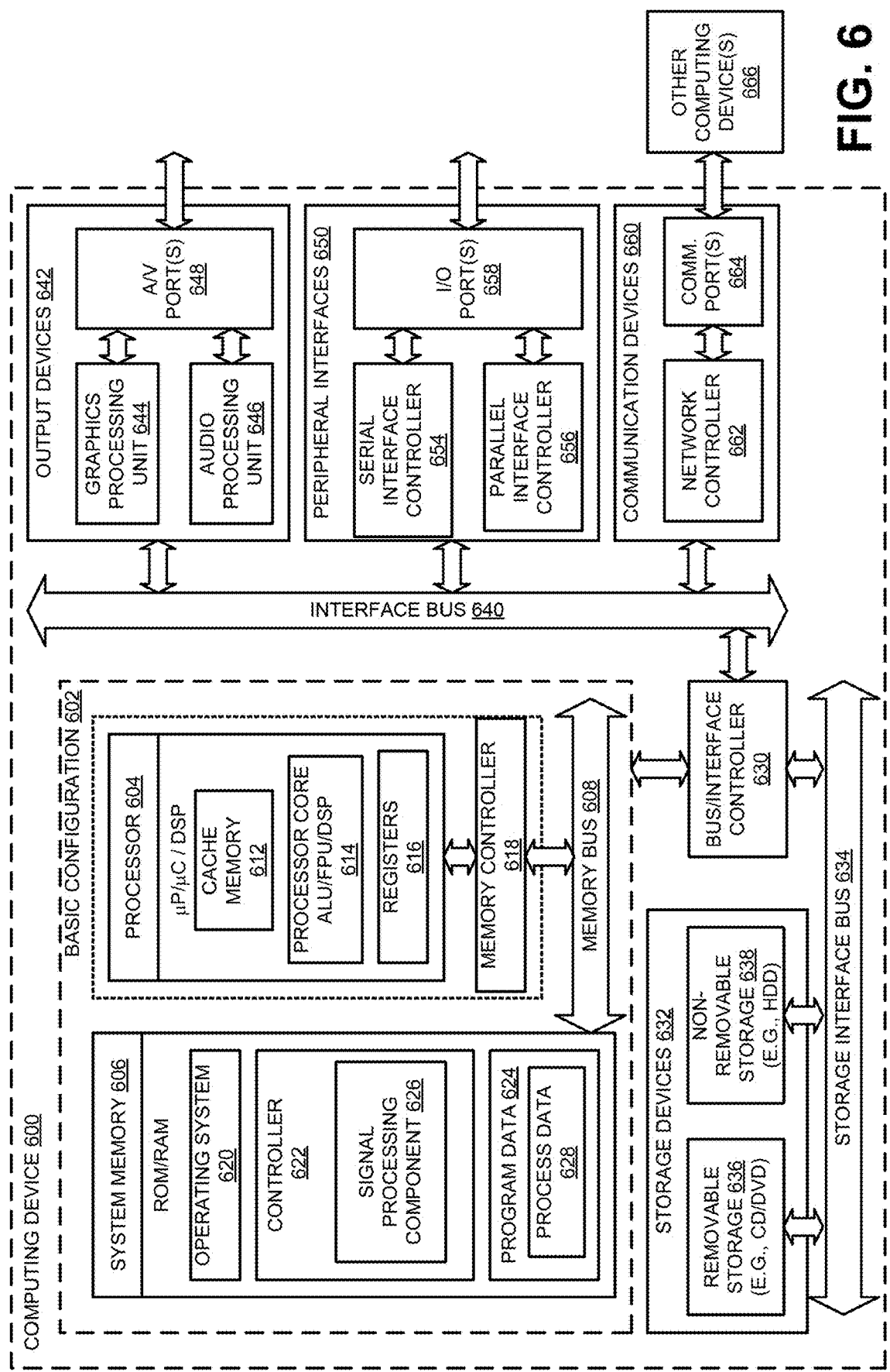
FIG. 6 illustrates a computing device, which may be used to control a system for normalized standard deviation transition based dosimetry monitoring of laser treatments.

FIG. 6 illustrates a computing device, which may be used to control a system for normalized standard deviation transition based dosimetry monitoring of laser treatments, arranged in accordance with at least some embodiments described herein.

In an example basic configuration 602, the computing device 600 may include one or more processors 604 and a system memory 606. A memory bus 608 may be used to communicate between the processor 604 and the system memory 606. The basic configuration 602 is illustrated in FIG. 6 by those components within the inner dashed line.

Depending on the desired configuration, the processor 604 may be of any type, including but not limited to a microprocessor (µP), a microcontroller (µC), a digital signal processor (DSP), or any combination thereof. The processor 604 may include one or more levels of caching, such as a cache memory 612, a processor core 614, and registers 616. The example processor core 614 may include an arithmetic logic unit (ALU), a floating point unit (FPU), a digital signal processing core (DSP core), or any combination thereof. An example memory controller 618 may also be used with the processor 604, or in some implementations, the memory controller 618 may be an internal part of the processor 604.

Depending on the desired configuration, the system memory 606 may be of any type including but not limited to volatile memory (such as RAM), non-volatile memory (such as ROM, flash memory, etc.) or any combination thereof. The system memory 606 may include an operating system 620, a controller 622, and program data 624. The controller 622 may include a signal processing component 626 to receive response signals corresponding to laser pulses directed to a treatment area as part of the laser treatment, determine a standard deviation following a receipt of each of the response signals, derive a normalized standard deviation by dividing the standard deviation by a mean of the response signals following the receipt of each response signal, and estimate a number of laser pulses remaining to complete the laser treatment for each response signal based on the normalized standard deviation following the receipt of each response signal. The program data 624 may include, among other data, process data 628 or the like, as described herein.

The computing device 600 may have additional features or functionality, and additional interfaces to facilitate communications between the basic configuration 602 and any desired devices and interfaces. For example, a bus/interface controller 630 may be used to facilitate communications between the basic configuration 602 and one or more data storage devices 632 via a storage interface bus 634. The data storage devices 632 may be one or more removable storage devices 636, one or more non-removable storage devices 638, or a combination thereof. Examples of the removable storage and the non-removable storage devices include magnetic disk devices such as flexible disk drives and hard-disk drives (HDDs), optical disk drives such as compact disc (CD) drives or digital versatile disk (DVD) drives, solid state drives (SSDs), and tape drives to name a few. Example computer storage media may include volatile and nonvolatile, removable and non-removable media implemented in any method or technology for storage of information, such as computer readable instructions, data structures, program modules, or other data.

The system memory 606, the removable storage devices 636 and the non-removable storage devices 638 are examples of computer storage media. Computer storage media includes, but is not limited to, RAM, ROM, EEPROM, flash memory or other memory technology, CD-ROM, digital versatile disks (DVDs), solid state drives, or other optical storage, magnetic cassettes, magnetic tape, magnetic disk storage or other magnetic storage devices, or any other medium which may be used to store the desired information and which may be accessed by the computing device 600. Any such computer storage media may be part of the computing device 600.

The computing device 600 may also include an interface bus 640 for facilitating communication from various interface devices (e.g., one or more output devices 642, one or more peripheral interfaces 650, and one or more communication devices 660) to the basic configuration 602 via the bus/interface controller 630. Some of the example output devices 642 include a graphics processing unit 644 and an audio processing unit 646, which may be configured to communicate to various external devices such as a display or speakers via one or more A/V ports 648. One or more example peripheral interfaces 650 may include a serial interface controller 654 or a parallel interface controller 656, which may be configured to communicate with external devices such as input devices (e.g., keyboard, mouse, pen, voice input device, touch input device, etc.) or other peripheral devices (e.g., printer, scanner, etc.) via one or more I/O ports 658. An example communication device 660 includes a network controller 662, which may be arranged to facilitate communications with one or more other computing devices 666 over a network communication link via one or more communication ports 664. The one or more other computing devices 666 may include servers at a datacenter, customer equipment, and comparable devices.

The network communication link may be one example of a communication media. Communication media may be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR) and other wireless media. The term computer readable media as used herein may include both storage media and communication media.

The computing device 600 may be implemented as a part of a general purpose or specialized server, mainframe, or similar computer that includes any of the above functions. The computing device 600 may also be implemented as a personal computer including both laptop computer and non-laptop computer configurations.

Figure 7:
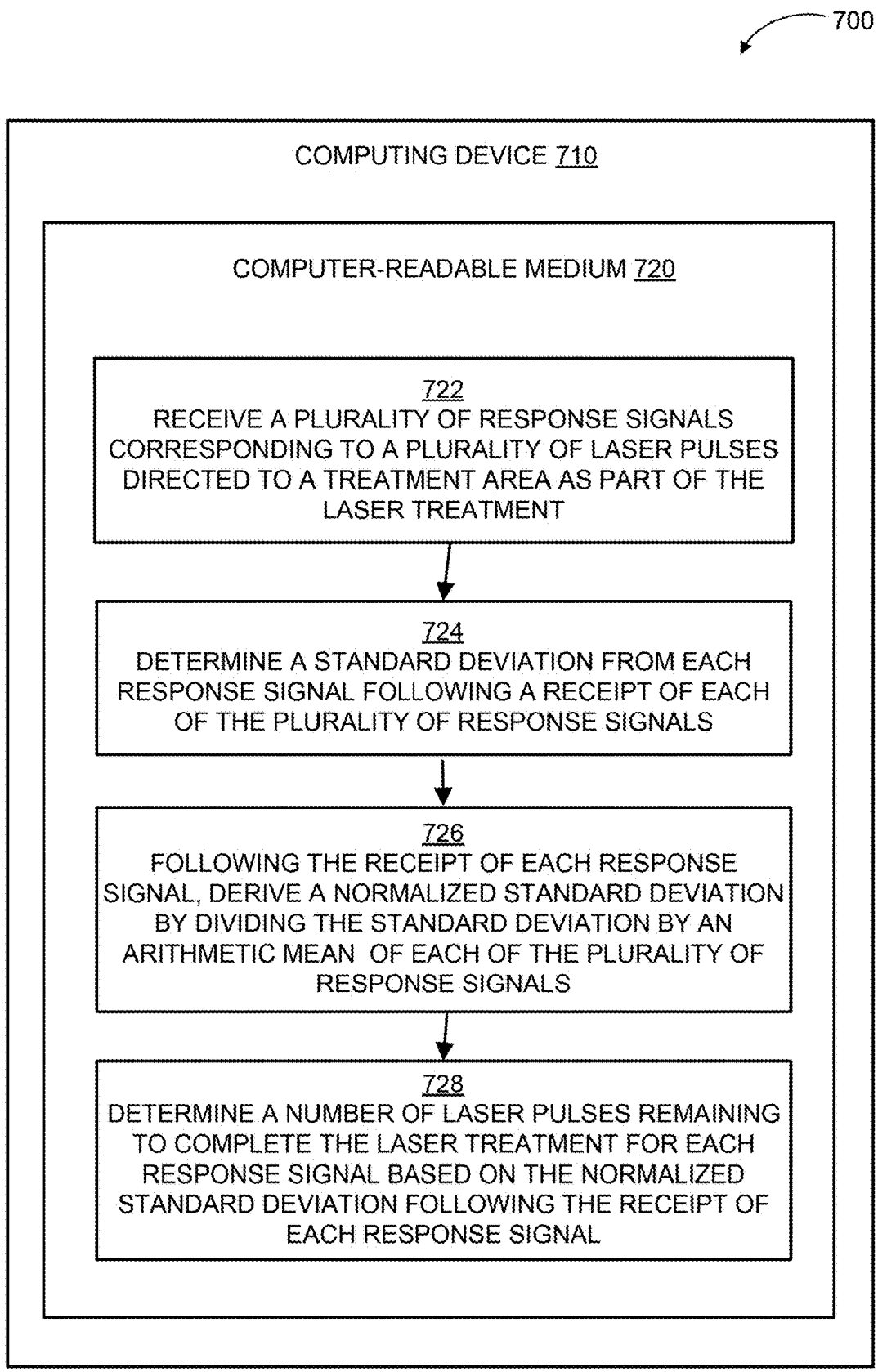
FIG. 7 is a flow diagram illustrating an example method to provide normalized standard deviation transition based dosimetry monitoring of laser treatments that may be performed by a computing device such as the computing device in FIG. 6.

FIG. 7 is a flow diagram illustrating an example method to provide normalized standard deviation transition based dosimetry monitoring of laser treatments that may be performed by a computing device such as the computing device in FIG. 6, arranged in accordance with at least some embodiments described herein.

Example methods may include one or more operations, functions, or actions as illustrated by one or more of blocks 722, 724, 726, and/or 728, and may in some embodiments be performed by a computing device such as the computing device 710 in FIG. 7. Such operations, functions, or actions in FIG. 7 and in the other figures, in some embodiments, may be combined, eliminated, modified, and/or supplemented with other operations, functions, or actions, and need not necessarily be performed in the exact sequence as shown. The operations described in the blocks 722-728 may also be implemented through execution of computer-executable instructions stored in a computer-readable medium such as a computer-readable medium 720 of a computing device 710.

An example process for normalized standard deviation transition based dosimetry monitoring for laser treatment may begin with block 722, "RECEIVE A PLURALITY OF RESPONSE SIGNALS CORRESPONDING TO A PLURALITY OF LASER PULSES DIRECTED TO A TREATMENT AREA AS PART OF THE LASER TREATMENT", where response signals derived from acoustically or optically detected physical responses to laser pulses applied to a treatment area may be received at a signal processor. The response signals may be in time domain and mixed with noise.

Block 722 may be followed by block 724, "DETERMINE A STANDARD DEVIATION FROM EACH RESPONSE SIGNAL FOLLOWING A RECEIPT OF EACH OF THE PLURALITY OF RESPONSE SIGNALS", where a standard deviation (sigma) value may be computed by the signal processor for each shot/treatment.

Block 724 may be followed by block 726, "FOLLOWING THE RECEIPT OF EACH RESPONSE SIGNAL, DERIVE A NORMALIZED STANDARD DEVIATION BY DIVIDING THE STANDARD DEVIATION BY AN ARITHMETIC MEAN OF EACH OF THE PLURALITY OF RESPONSE SIGNALS", where the normalized standard deviation (sigma-norm) may be computed by dividing the standard deviation by an arithmetic mean. In other examples, a geometric mean, a median, or other normalizing attribute may be used.

Block 726 may be followed by block 728, "DETERMINE A NUMBER OF LASER PULSES REMAINING TO COMPLETE THE LASER TREATMENT FOR EACH RESPONSE SIGNAL BASED ON THE NORMALIZED STANDARD DEVIATION FOLLOWING THE RECEIPT OF EACH RESPONSE SIGNAL", where the number of laser pulse for completion of the treatment may be estimated based on the normalized standard deviation metric. As the metric represents a change (transition) in the sigma value, the estimation may be stable despite high noise levels, response signal variations, or even applied laser pulse power variations.

The operations included in process 700 are for illustration purposes. Normalized standard deviation transition based dosimetry monitoring for laser treatment may be implemented by similar processes with fewer or additional operations, as well as in different order of operations using the principles described herein. The operations described herein may be executed by one or more processors operated on one or more computing devices, one or more processor cores, specialized processing devices, and/or general purpose processors, among other examples.

FIG. 8 illustrates a block diagram of an example computer program product, some of which are arranged in accordance with at least some embodiments described herein.

In some examples, as shown in FIG. 8, a computer program product 800 may include a signal-bearing medium 802 that may also include one or more machine readable instructions 804 that, in response to execution by, for example, a processor may provide the functionality described herein. Thus, for example, referring to the processor 604 in FIG. 6, the controller 622 may perform or control performance of one or more of the tasks shown in FIG. 8 in response to the instructions 804 conveyed to the processor 604 by the signal-bearing medium 802 to perform actions associated with normalized standard deviation transition based dosimetry monitoring for laser treatment as described herein. Some of those instructions 804 may include, for example, one or more instructions to receive a plurality of response signals corresponding to a plurality of laser pulses directed to a treatment area as part of the laser treatment; determine a standard deviation following a receipt of each of the plurality of response signals; following the receipt of each response signal, derive a normalized standard deviation by dividing the standard deviation by an arithmetic mean of the plurality of response signals; and determine a number of laser pulses remaining to complete the laser treatment for each response signal based on the normalized standard deviation following the receipt of each response signal according to some embodiments described herein.

In some implementations, the signal-bearing medium 802 depicted in FIG. 8 may encompass computer-readable medium 806, such as, but not limited to, a hard disk drive (HDD), a solid state drive (SSD), a compact disc (CD), a digital versatile disk (DVD), a digital tape, memory, etc. In some implementations, the signal-bearing medium 802 may encompass recordable medium 808, such as, but not limited to, memory, read/write (R/W) CDs, R/W DVDs, etc. In some implementations, the signal-bearing medium 802 may encompass communications medium 810, such as, but not limited to, a digital and/or an analog communication medium (e.g., a fiber optic cable, a waveguide, a wired communication link, a wireless communication link, etc.). Thus, for example, the computer program product 800 may be conveyed to one or more modules of the processor 604 by an RF signal bearing medium, where the signal-bearing medium 802 is conveyed by the communications medium 810 (e.g., a wireless communications medium conforming with the IEEE 802.11 standard).

According to some examples, a method for normalized standard deviation transition based dosimetry monitoring of a laser treatment is described. The method may include receiving a plurality of response signals corresponding to a plurality of laser pulses directed to a treatment area as part of the laser treatment; determining a standard deviation from each response signal following a receipt of each of the plurality of response signals; deriving a normalized standard deviation by dividing the standard deviation by an arithmetic mean of each of the plurality of response signals following the receipt of each response signal; and determining a number of laser pulses remaining to complete the laser treatment for each response signal based on the normalized standard deviation following the receipt of each response signal.

According to other examples, determining the number of laser pulses remaining to complete the laser treatment for each response signal may include determining the number of laser pulses remaining to complete the laser treatment based on a change in the normalized standard deviation between two consecutive response signals. The method may further include removing a first response signal from the determination of the standard deviation and the arithmetic mean. Receiving the plurality of response signals corresponding to the plurality of laser pulses directed to the treatment area may include detecting a response from the treatment area upon application of a laser pulse to the treatment area; and deriving a response signal from the detected response.

According to further examples, detecting the response from the treatment area may include acoustically detecting the response. Detecting the response from the treatment area may include detecting the response through opto-reflectometry. The method may further include automatically controlling a laser source that directs the plurality of laser pulses to the treatment area to cease direction of laser pulses upon completion of the laser treatment based on the remaining number of laser pulses. The method may also include performing a state based analysis of a change in the normalized standard deviation. Performing the state based analysis of the change in the normalized standard deviation may include performing a Markov state based analysis or a Bayesian state based analysis. Performing the state based analysis of the change in the normalized standard deviation may include generating an entropy-based decision tree based on the normalized standard deviation to determine the number of laser pulse remaining for the completion of the laser treatment. Determining the standard deviation of each of the plurality of response signals may include determining the standard deviation following the receipt of each of the plurality of response signals in time domain.

According to other examples, an apparatus for normalized standard deviation transition based dosimetry monitoring of a laser treatment is described. The apparatus may include a detector configured to detect a plurality of responses from a treatment area upon application of a plurality of laser pulses to the treatment area as part of the laser treatment and derive a plurality of response signals from the plurality of responses corresponding to the plurality of laser pulses directed to the treatment area. The apparatus may further include a processor coupled to the detector and configured to determine a standard deviation from each response signal following a receipt of each of the plurality of response signals; following the receipt of each response signal, derive a normalized standard deviation by dividing the standard deviation by an arithmetic mean of each of the plurality of response signals; and determine a number of laser pulses remaining to complete the laser treatment following the receipt of each response signal based on the normalized standard deviation.

According to some examples, the processor may be configured to determine the number of laser pulses remaining to complete the laser treatment based on a change in the normalized standard deviation between two consecutive response signals. The processor may be further configured to remove a first response signal from the determination of the standard deviation and the arithmetic mean. The detector may be configured to detect the plurality of responses from the treatment area through acoustic detection. The detector may also be configured to detect the plurality of responses from the treatment area through opto-reflectometry. The processor may be further configured to provide instructions to a laser source that directs the plurality of laser pulses to the treatment area to cease direction of laser pulses upon completion of the laser treatment based on the remaining number of laser pulses.

According to other examples, the processor may be further configured to perform a state based analysis of a change in the normalized standard deviation. The processor may be configured to perform the state based analysis of the change in the normalized standard deviation through a Markov state based analysis or a Bayesian state based analysis. The processor may be configured to perform the state based analysis of the change in the normalized standard deviation through generation of an entropy-based decision tree based on the normalized standard deviation to determine the number of laser pulse remaining for the completion of the laser treatment. The processor may be configured to determine the standard deviation following the receipt of each of the plurality of response signals in time domain. The treatment area may be an eye.

According to further examples, a laser treatment system for normalized standard deviation transition based dosimetry monitoring is described. The system may include a laser source configured to direct a plurality of laser pulses to a treatment area as part of a laser treatment and a detector configured to detect a plurality of responses from the treatment area upon application of the plurality of laser pulses to the treatment area; and derive a plurality of response signals from the plurality of responses corresponding to the plurality of laser pulses directed to the treatment area. The system may also include an estimator coupled to the detector and configured to determine a standard deviation from each response signal following a receipt of each of the plurality of response signals; following the receipt of each response signal, derive a normalized standard deviation by dividing the standard deviation by an arithmetic mean of each of the plurality of response signals; and determine a number of laser pulses remaining to complete the laser treatment for each response signal based on the normalized standard deviation following the receipt of each response signal.

According to some examples, the processor may be further configured to provide instructions to the laser source to cease direction of laser pulses upon completion of the laser treatment based on the remaining number of laser pulses. The estimator may be configured to determine the number of laser pulses remaining to complete the laser treatment based on a change in the normalized standard deviation between two consecutive response signals. The estimator may be further configured to remove a first response signal from the determination of the standard deviation and the arithmetic mean. The detector may be configured to detect the plurality of responses from the treatment area through acoustic detection. The detector may be configured to detect the plurality of responses from the treatment area through opto-reflectometry. The estimator may be further configured to perform a state based analysis of a change in the normalized standard deviation.

According to other examples, the estimator may be configured to perform the state based analysis of the change in the normalized standard deviation through a Markov state based analysis or a Bayesian state based analysis. The estimator may be configured to perform the state based analysis of the change in the normalized standard deviation through generation of an entropy-based decision tree based on the normalized standard deviation to determine the number of laser pulse remaining for the completion of the laser treatment. The estimator may be configured to determine the standard deviation following the receipt of each of the plurality of response signals in time domain. The treatment area may be an eye.

There are various vehicles by which processes and/or systems and/or other technologies described herein may be effected (e.g., hardware, software, and/or firmware), and the preferred vehicle will vary with the context in which the processes and/or systems and/or other technologies are deployed. For example, if an implementer determines that speed and accuracy are paramount, the implementer may opt for mainly hardware and/or firmware vehicle; if flexibility is paramount, the implementer may opt for mainly software implementation; or, yet again alternatively, the implementer may opt for some combination of hardware, software, and/or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, each function and/or operation within such block diagrams, flowcharts, or examples may be implemented, individually and/or collectively, by a wide range of hardware, software, firmware, or virtually any combination thereof. In one embodiment, several portions of the subject matter described herein may be implemented via application specific integrated circuits (ASICs), field programmable gate arrays (FPGAs), digital signal processors (DSPs), or other integrated formats. However, some aspects of the embodiments disclosed herein, in whole or in part, may be equivalently implemented in integrated circuits, as one or more computer programs executing on one or more computers (e.g., as one or more programs executing on one or more computer systems), as one or more programs executing on one or more processors (e.g., as one or more programs executing on one or more microprocessors), as firmware, or as virtually any combination thereof, and designing the circuitry and/or writing the code for the software and/or firmware are possible in light of this disclosure.

The present disclosure is not to be limited in terms of the particular embodiments described in this application, which are intended as illustrations of various aspects. Many modifications and variations can be made without departing from its spirit and scope. Functionally equivalent methods and apparatuses within the scope of the disclosure, in addition to those enumerated herein, are possible from the foregoing descriptions. Such modifications and variations are intended to fall within the scope of the appended claims. The present disclosure is to be limited only by the terms of the appended claims, along with the full scope of equivalents to which such claims are entitled. It is also to be understood that the terminology used herein is for the purpose of describing particular embodiments only, and is not intended to be limiting.

In addition, the mechanisms of the subject matter described herein are capable of being distributed as a program product in a variety of forms, and an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive (HDD), a compact disc (CD), a digital versatile disk (DVD), a digital tape, a computer memory, a solid state drive (SSD), etc.; and a transmission type medium such as a digital and/or an analog communication medium (e.g., a fiber optic cable, a waveguide, a wired communication link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein may be integrated into a data processing system via a reasonable amount of experimentation. A data processing system may include one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors.

A data processing system may be implemented utilizing any suitable commercially available components, such as those found in data computing/communication and/or network computing/communication systems. The herein described subject matter sometimes illustrates different components contained within, or connected with, different other components. Such depicted architectures are merely exemplary, and in fact, many other architectures may be implemented which achieve the same functionality. In a conceptual sense, any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermediate components. Likewise, any two components so associated may also be viewed as being "operably connected", or "operably coupled", to each other to achieve the desired functionality, and any two components capable of being so associated may also be viewed as being "operably couplable", to each other to achieve the desired functionality. Specific examples of operably couplable include but are not limited to physically connectable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). If a specific number of an introduced claim recitation is intended, such an intent will be explicitly recited in the claim, and in the absence of such recitation, no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations).

Furthermore, in those instances where a convention analogous to "at least one of A, B, and C, etc." is used, in general, such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

For any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments are possible. The various aspects and embodiments disclosed herein are for purposes of illustration and are not intended to be limiting, with the true scope and spirit being indicated by the following claims.

What is claimed is:

1. An apparatus for normalized standard deviation transition based dosimetry monitoring of a laser treatment, the apparatus comprising:
    a detector configured to:
    detect a plurality of responses from a treatment area upon sequentially applying a plurality of laser pulses to the treatment area as part of the laser treatment; and
    derive a plurality of response signals from the plurality of responses corresponding to the plurality of laser pulses sequentially directed to the treatment area; and
    a processor coupled to the detector, the processor configured to:
    determine a standard deviation from each response signal following a receipt of each of the plurality of response signals;
    derive a normalized standard deviation by dividing the standard deviation by an arithmetic mean of each of the plurality of response signals;
    detect normalized standard deviation transition based on a change in the normalized standard deviations of two consecutive response signals among the plurality of response signals; and determine a number of laser pulses remaining to complete the laser treatment upon detecting the normalized standard deviation transition, the number of laser pulses being greater than 0.

2. The apparatus of claim 1, wherein the processor is further configured to:
    remove a first response signal from the determination of the standard deviation and the arithmetic mean.

3. The apparatus of claim 1, wherein the detector is configured to detect the plurality of responses from the treatment area through acoustic detection or opto-reflectometry.

4. The apparatus of claim 1, wherein, the processor is configured to further determine the number of laser pulses by performing a state based analysis of a change in the normalized standard deviation through one or more of a Markov state based analysis, a Bayesian state based analysis, or generation of an entropy-based decision tree based on the normalized standard deviation.

5. The apparatus of claim 1, wherein the processor determines the standard deviation in a time domain.

6. The apparatus of claim 1, wherein the treatment area is an eye.

* * * * *